United States Patent
Grossman et al.

(10) Patent No.: US 7,019,831 B2
(45) Date of Patent: Mar. 28, 2006

(54) SEPARATION DEVICE SUBSTRATE INCLUDING NON-FLUORESCENT QUENCHER DYE

(75) Inventors: Paul D. Grossman, Hillsborough, CA (US); Jeffery D. Frazier, Portola Valley, CA (US); Ian Harding, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 288 days.

(21) Appl. No.: 10/623,913

(22) Filed: Jul. 21, 2003

(65) Prior Publication Data

US 2004/0053404 A1    Mar. 18, 2004

Related U.S. Application Data

(60) Continuation-in-part of application No. 10/455,986, filed on Jun. 7, 2003, which is a division of application No. 09/938,767, filed on Aug. 24, 2001, now Pat. No. 6,627,433.

(51) Int. Cl.
G01J 3/30 (2006.01)
G01N 21/01 (2006.01)
G01N 1/10 (2006.01)

(52) U.S. Cl. .................. 356/318; 356/344; 356/246

(58) Field of Classification Search .......... 356/318, 356/344; 204/450, 601, 603; 435/288.2, 435/288.4, 288.7
See application file for complete search history.

(56) References Cited

U.S. PATENT DOCUMENTS

| | | | |
|---|---|---|---|
| 4,832,815 A | 5/1989 | Kambara et al. | |
| 5,114,551 A | 5/1992 | Hjerten et al. | |
| 5,192,412 A | 3/1993 | Kambara et al. | |
| 5,268,080 A | 12/1993 | Kambara et al. | |
| 5,277,780 A | 1/1994 | Kambara | |
| 5,314,602 A | 5/1994 | Kambara et al. | |
| 5,439,578 A | 8/1995 | Dovichi et al. | |
| 5,498,324 A * | 3/1996 | Yeung et al. | 204/452 |
| 5,529,679 A | 6/1996 | Takahashi et al. | |
| 5,552,028 A | 9/1996 | Madabhushi et al. | |
| 5,582,705 A | 12/1996 | Yeung et al. | |
| 5,695,626 A | 12/1997 | Yeung et al. | |
| 5,741,411 A | 4/1998 | Yeung et al. | |
| 5,790,727 A | 8/1998 | Dhadwal et al. | |
| 5,833,827 A | 11/1998 | Anazawa et al. | |

(Continued)

FOREIGN PATENT DOCUMENTS

EP    0 840 115    5/1998

OTHER PUBLICATIONS

Huang et al., *Acousto-Optical Deflection-Based Laser Beam Scanning for Fluorescence Detection on Mulitchannel Electrophoretic Microships*, Anal. Chem., vol. 71, No. 23, pp. 5309-5314 (1999).

(Continued)

*Primary Examiner*—Gregory J. Toatley, Jr.
*Assistant Examiner*—Sarah J. Chisdes
(74) *Attorney, Agent, or Firm*—Kilyk & Bowersox, P.L.L.C.

(57) ABSTRACT

A device is provided for the analysis of samples. The device includes a plurality of sample-containment features and a non-fluorescent quenching material for minimizing crosstalk between optical signals emitted from or directed toward the sample-containment features.

41 Claims, 4 Drawing Sheets

U.S. PATENT DOCUMENTS

| | | | |
|---|---|---|---|
| 5,867,266 A | | 2/1999 | Craighead |
| 5,910,287 A | * | 6/1999 | Cassin et al. ............... 422/102 |
| 6,017,434 A | * | 1/2000 | Simpson et al. ............ 204/612 |
| 6,027,695 A | * | 2/2000 | Oldenburg et al. ......... 422/102 |
| 6,159,353 A | | 12/2000 | West et al. |
| 6,171,780 B1 | * | 1/2001 | Pham et al. ................... 435/4 |
| 6,236,945 B1 | | 5/2001 | Simpson et al. |
| 6,246,046 B1 | | 6/2001 | Landers et al. |
| 6,413,782 B1 | * | 7/2002 | Parce et al. ................. 436/514 |
| 6,906,797 B1 | * | 6/2005 | Kao et al. ................... 356/317 |
| 2002/0003091 A1 | * | 1/2002 | Kojima et al. ............. 204/603 |
| 2002/0176804 A1 | * | 11/2002 | Strand et al. ............... 422/100 |
| 2003/0190608 A1 | * | 10/2003 | Blackburn ..................... 435/6 |
| 2004/0026252 A1 | * | 2/2004 | Li .............................. 204/603 |

OTHER PUBLICATIONS

Wang et al., *Microfabricated Electrophoresis Chips for Simultaneous Bioassays of Glucose, Uric Acid, Ascorbic Acid, and Acetaminophen*, Anal. Chem., vol. 72, No. 11, pp. 2514-2518 (2000).

Cheng et al., *Development of a Multichannel Microfluidic Analysis System Employing Affinity Capillary Electrohoresis for Immunoassay*, Anal. Chem., vol. 73, No. 7, pp. 1472-1479 (2001).

Tian et al. *Capillary and Microchip Electrophoresis for Rapid Detection of Known Mutations by Combining Alle-Specific DNA Amplification with Heteroduplex Analysis*, Clinical Chem., vol. 47, No. 2, pp. 173-185 (2001).

* cited by examiner

SEPARATION DEVICE SUBSTRATE INCLUDING NON-FLUORESCENT QUENCHER DYE

CROSS REFERENCE TO RELATED APPLICATION

This application is a continuation-in-part application of U.S. patent application Ser. No. 10/455,986, filed Jun. 7, 2003, which is a divisional of U.S. patent application Ser. No. 09/938,767, filed Aug. 24, 2001 now U.S. Pat. No. 6,627,433, both of which are incorporated herein in their entireties by reference.

FIELD

The present invention relates to a multi-channel analyte-separation device.

REFERENCES

Backhouse et al., "DNA sequencing in a monolithic microchannel device," Electrophoresis 2000, 21, 150–156.

Dolnik et al., "Capillary electrophoresis on microchip," Electrophoresis 2000, 21, 41–54.

Grossman and Colburn, "Capillary Electrophoresis Theory and Practice," Chapter 1, Academic Press (1992).

Kambara et al., U.S. Pat. No. 5,192,142 (1993).

Madabhushi et al., U.S. Pat. No. 5,552,028 (1996).

Sambrook et al., eds., "Molecular Cloning: A Laboratory Manual," Second Edition, Chapter 5, Cold Spring Harbor Laboratory Press (1989).

Woolley et al., "Ultra-high-speed DNA fragment separations using microfabricated capillary array electrophoresis chips," Proc. Natl. Acad. Sci., vol. 91, pp. 11348–11352, November 1994, Biophysics.

Yeung et al., U.S. Pat. Nos. 5,741,411 and 5,582,705.

BACKGROUND

Devices for carrying out separations of analytes, such as biomolecules, for example, proteins, DNA, RNA, and the like, have gained widespread use in recent years.

In electrophoretic separations, it is often desirable to illuminate a plurality of migrating analytes, tagged with excitable reporters (for example, fluorescent dyes), to stimulate detectable emission indicative of the nature (for example, identity or composition) of the tagged analytes.

SUMMARY

According to various embodiments, an analyte detection device is provided that includes a substrate defining an array of channels, wells, vials, or the like, wherein the substrate includes a light-absorbing or light-quenching material. The light-absorbing and/or light-quenching material can be in the form of a quencher dye or pigment composited or mixed with the substrate material or provided as a separate layer coated on top of a base substrate material. The light-absorbing and/or light-quenching material is referred to herein as a non-fluorescent quencher. According to various embodiments, adjacent channels or wells of the device are separated by respective wall structures. Each wall structure can include at least a portion that is substantially transparent. The transparent portions can be disposed along a beam path or line that intersects or crosses (for example, is substantially co-planar and substantially normal to) the longitudinal axes of the channels, for example, adjacent or near one end of each channel.

According to various embodiments, a system can be provided that includes an excitation-beam source, for example, a laser, that can be adapted to direct an excitation beam along the beam path, such that the beam can simultaneously pass through each of the transparent portions and each of the channels, wells, vials, or the like. Plural samples in various channels, wells, vials, or the like can thus be simultaneously irradiated and detected.

According to various embodiments, methods are provided for sequencing biomolecules (for example, DNA, RNA, PNA, or the like) or other analysis methods in which each of a plurality of different nucleic acid sequence fragment types is labeled with a spectrally distinctive emitting or fluorescing dye. According to various embodiments, a side-entry laser arrangement is provided at a detection zone of a multi-channel electrophoresis device, and the arrangement excites dyes, while in respective channels, causing them to excite and emit detectable emission beams.

According to various embodiments, light emitted from samples in the respective channels can pass through a laser light filter, through a collection lens, through a transmission dispersion element that spectrally separates the light, and/or through a focusing lens. Focused light can be directed to be incident on a detector array (for example, a CCD) capable of detecting the simultaneously spatially focused and spectrally divergent light from the detection regions of all the channels. Electronic signals from the detector array can provide information about the character or sequence of the DNA sample. The laser light can impinge on a sample in each channel by passing through a substantially transparent region of each channel, or by passing through a groove transverse to and passing through each channel. Stray light, and extraneous light can be absorbed by the light-quenching or light-absorbing material in or on the substrate so as not to interfere with excitation or detection.

BRIEF DESCRIPTION OF THE DRAWINGS

The structure and manner of operation according to the present teachings can further be understood by reference to the following description taken in conjunction with the accompanying drawings, in which identical reference numerals identify identical or similar elements, and in which.

Figure 1:
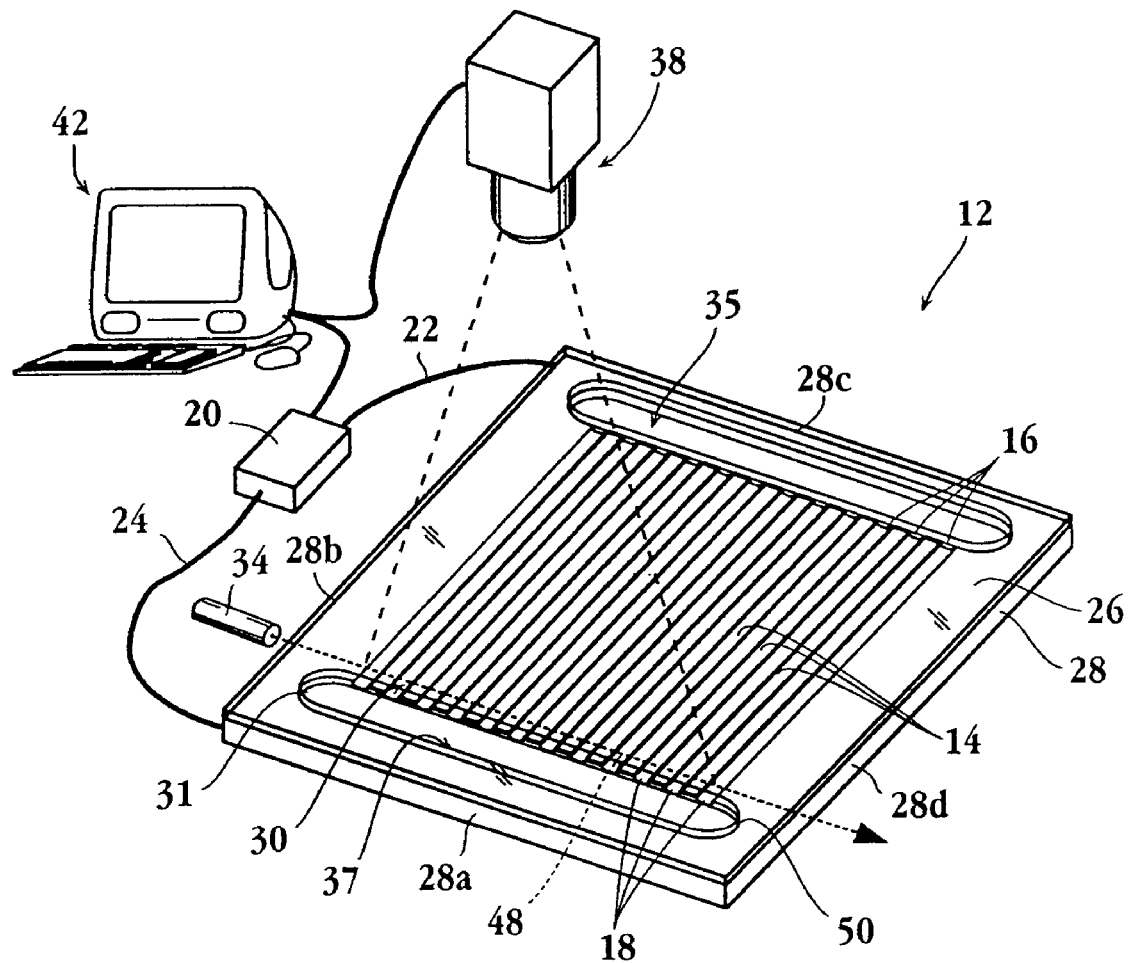
FIG. 1 is a perspective view from above of an electrophoresis system, showing a multi-channel analyte-separation device including a plurality of separation channels, a detection zone, an excitation beam source, an optical detection system, and a programmed computer control/analysis system, according to various embodiments.

Other various embodiments of the present teachings will be apparent to those skilled in the art from consideration of the specification and practice of the devices, systems, and methods described herein, and the detailed description that follows. It is intended that the specification and examples be considered as exemplary only.

DETAILED DESCRIPTION

Unless stated otherwise, the following terms and phrases as used herein are intended to have the following meanings:

The term "channel" as used herein refers to an elongate, narrow passage or other structure, for example, a groove, formed in a substrate and capable of supporting a volume of separation medium and/or buffer solution, for example, such as is used in carrying out electrophoresis. The geometry of a channel can vary widely. For example, a channel can have a circular, oval, semi-circular, semi-oval, triangular, rectangular, square, or other cross-section, or a combination thereof. Channels can be fabricated by a wide range of technologies, including microfabrication techniques. As used herein, the term "channel' is not intended to encompass a capillary tube.

The terms "capillary" and "capillary tube" as used herein refer to an elongated tubular or cylindrical structure defining an inner lumen. For example, a capillary can be an elongated capillary or micro-capillary tube made, for example, from fused silica, quartz, silicate-based glass, such as borosilicate glass, phosphate glass, alumina-containing glass, and the like, or other silica-like material(s). As used herein, "capillary" does not encompass a channel in a substrate such as a plate, slide, chip, wafer, or the like.

The term "separation unit" as used herein can refer to any device adapted to separate a sample including nucleic acid or amino acid polymers. The separate unit can be, for example, a channel or capillary.

The term "channel device" refers to a substrate, such as a plate, slide, chip, wafer, or similar structure, including one or more channels, for example, grooves. A channel device can be adapted, at least in part, for carrying out electrophoresis. Channel devices can take the form, for example, of microfabricated devices for example, a plate, a slide, a chip, a wafer, or other substrate that is grooved, etched, or fluted.

The term "well" as used herein refers to a tubular, cylindrical, or rounded structure having an open end and a closed end. One or both ends can be tapered, for example. The well can be sealed by, for example, placing a sealing film over the open end of the well. A plurality of wells can be sealed using a single film. For example, a plurality of wells can be fixed to a plate. The plate can be adapted to be placed in the detector device or can be fixed to the detector device. The plate can include, for example, 96 wells, 284 wells, or the like.

The term "vial" as used herein refers to a tubular or cylindrical structure having an open end and a closed end. The vial can be sealed with, for example, a cap secured to the open end of the vial. A plurality of vials can be placed in the detection device. A plurality of vials can be placed in a holder or template that is adapted to be placed in the detection device.

As used herein, the terms "sample zone" and "analyte zone" refer to a collection of molecules comprising a subset of sample or analyte components having similar electrophoretic migration velocities such that the molecules of a sample zone or analyte zone migrate as a defined zone. A zone can be made up of molecules having identical electrophoretic migration velocities. Sample zones and analyte zones are often referred to as "bands."

As used herein, the terms "separation medium" and "separation matrix" refer to a medium in which an electrophoretic separation of sample components can take place. Separation media typically comprise several components, at least one of which is a charge-carrying component, or electrolyte. The charge-carrying component can be part of a buffer system for maintaining the separation medium at a defined pH. Media for separating polynucleotides, proteins, or other biomolecules, having different sizes but identical charge-frictional drag ratios in free solution, can further include a sieving component. The sieving component can be composed of a cross-linked polymer gel, for example, a cross-linked polyacrylamide, a cross-linked agarose (Sambrook), or a polymer solution, for example, a solution of polyacrylamide, hydroxyethyl cellulose, and the like (Grossman; Madabhushi).

By way of example, a capillary array will be described. However, the present teachings should not be so limiting. The teachings contained herein can be used with, for example, devices found in FIGS. 2–24 of U.S. Pat. No. 6,159,368, which is incorporated herein by reference in its entirety.

According to various embodiments, channel devices are provided that are useful, for example, in electrophoretic separations of bio-molecules. According to various embodiments, the channel devices can employ side-entry excitation geometry. Channel devices herein are to be contrasted with capillary arrangements that employ multiple capillaries, that is, elongated tubular structures. The channel devices herein can be comprised of a substrate, such as a plate, slide, chip, wafer, or similar structure, including one or more channels (for example, grooves) and a light-absorbing or light-quenching material disposed in or on the substrate. According to various embodiments, channel devices can take the form, for example, of microfabricated devices, for example, a plate, a slide, a chip, a wafer, or other substrate, that is grooved, etched, or fluted. It has previously been suggested by others that channel-device technology was not well developed enough to employ side-entry illumination (See Yeung et al., U.S. Pat. No. 5,741,411, Col. 8, lines 14–24, and U.S. Pat. No. 5,582,705, Col. 8, lines 9–19).

According to various embodiments, a channel device, not a capillary tube device, is provided. The channel device can include a substrate with a plurality of channels formed in the substrate, and a light-absorbing or light-quenching material dispersed in or on the substrate. The light-absorbing or light-quenching material can be dispersed, mixed, or dissolved in the substrate material, for example, to be homogeneously or uniformly disposed throughout the substrate material. According to various embodiments, the light-absorbing or light-quenching material can be in the form of a coating or layer disposed on one or more surfaces of the substrate. The coating or layer can be formed on the substrate or pre-formed and then applied to the substrate. Each channel can include an inlet end and an outlet end. The channels can be disposed in spaced relation relative to one another, with each adjacent pair of channels being separated by a respective portion of the substrate that includes at least one region that is substantially transparent. An excitation-beam source can be adapted to direct a beam of coherent light along a beam path that intersects each of the channels at a region that is substantially transparent between the inlet and outlet ends.

According to various embodiments, each channel can include opposed sidewalls with portions that are substantially parallel to one another. The parallel portions can include at least a portion that is at least partially transparent, for example, transparent. The beam path can extend through the partially transparent, parallel portions of the sidewalls. Such construction can avoid or reduce loss of light intensity as the beam travels through the device from channel to channel. The side walls of the channels can be coated or layered with a coating or layer of light-absorbing or light-quenching material, except at the transparent portion.

According to various embodiments, a transverse channel can be formed in the substrate such that the transverse channel passes through each of the plurality of channels in the substrate. The beam path can extend through the transverse channel, thereby passing through at least a portion of each of the plurality of channels. Such construction can avoid or reduce loss of light intensity as the beam passes through the device from channel to channel.

According to various embodiments, separation channels can be formed on a glass or plastic substrate, such as a plate, slide, wafer, chip, or the like, by microfabrication techniques known in the art, for example, photolitho and/or wet-chemical etching procedures, laser ablation, electroforming, microcontact printing, microstamping, micromolding, microcasting, micromachining, engraving, embossing techniques, and/or casting in a polymer, and the like. For example, Backhouse et al., Dolnik et al., and Woolley et al., each of which is incorporated herein in its entirety by reference, each discusses fabrication techniques that the skilled artisan can employ in making the devices described herein.

According to various embodiments, the separation channels can be formed in a generally planar substrate comprised at least in part, for example, of an electrically insulating material, for example, fused silica, quartz, silicate-based glass, such as borosilicate glass, phosphate glass, alumina-containing glass, and the like, or other silica-like material(s) The substrate can be a plastic or polymeric material, for example, a polyolefin, a polycarbonate, a polyethylene terephthalate, an acrylic, a polyacrylate, a siloxane, or a comonomer thereof. The substrate can be formed with or without channels by any standard technique, including molding, casting, masking, chemical vapor deposition, etching, lithography, soft lithography, or other forming or depositing techniques. Methods of forming a substrate as taught in the art can be used, such as, for example, the methods taught in U.S. Pat. No. 6,017,434, issued Jan. 25, 2000, which is incorporated herein in its entirety by reference.

The channel devices described herein can be well suited, for example, to fluorescence detection of a fluorescent target species in a sample. According to various embodiments, channels of a channel device can be arranged in a coplanar channel array. The channel array can include at least about 4 (for example, 8, 12, 16, 24, 48, 96, or more) coplanar, adjacently-arranged channels. Each channel can have one or more sidewall that, in combination with a base, forms the channel. Additionally, each channel can have a ceiling, for example, a glass plate, a polymeric plate, or a polymer film. The ceiling can include a light-absorbing or light-quenching material disposed therein or thereon, and the ceiling can be a part of the substrate or a separate component. The ceiling can include one or more transparent regions or areas. One or more regions of each sidewall of each channel can include one or more transparent portions. A transparent portion is transparent to light having a wavelength about equal to a wavelength of a beam of coherent light used to irradiate a target species in a channel. A "transparent portion" or "transparent medium" is one that transmits light with little or no attendant light scattering or absorption. For example, a transparent portion can be comprised of an optically clear glass or plastic. According to various embodiments, the transparent portion can be transparent to light having a wavelength of about 200–1500 nm; for example, about 250–800 nm.

Together, the transparent portions of the sidewalls can define a transparent substantially linear optical path extending through the channel array, for example, from one channel to the next all the way through the channel array. The transparent path can comprise a plane extending through all the channels, for example, where the channels are fabricated entirely out of transparent material.

The transparent portions of the sidewalls can exhibit little or no fluorescence when exposed to a beam of coherent light, so as to reduce or eliminate background fluorescence from the detected fluorescence. For example, the transparent portions can be selected and designed to exhibit substantially no fluorescence when exposed to light having a wavelength of from about 200 to about 1500 nm, for example, from about 250 to about 800 nm. The phrase "substantially no fluorescence" means that the level of fluorescence emitted, if any, by a transparent portion is less than an observed background fluorescence.

According to various embodiments, a target species can be detected in a respective channel through a transparent portion provided in an upper portion of the channel sidewall or in a portion of a ceiling of the channel. Such an additional transparent portion can be selected and designed to exhibit substantially no fluorescence when exposed to light having a wavelength about equal to the wavelength of light emitted by a fluorescing target species. The entire channel device can be constructed from a transparent, non-fluorescing material, for example, fused silica. Transparent windows can alternatively be formed at or along one or more selected regions of one or more sidewall, ceiling, bottom, or combination thereof, of one or more channels.

Instead of, or in addition to, utilizing such transparent portions, one or more sidewalls can include a translucent portion defining a translucent linear path extending through the array perpendicular to the channels. A translucent medium can produce some light scattering when transmitting light. Transparency can be preferred over translucency because of greater light throughput and reduced detection signal-to-noise ratio (S/N).

As indicated above, side-entry irradiation of target species in multiple channels can be effected through a transparent portion of a sidewall of each channel in a multichannel array. According to various embodiments, light can pass through the transparent portions in the array in a sequential manner. A coherent light source can be positioned to direct a beam of coherent light along the transparent path. A coherent light source can produce light waves traveling together in phase. The light can have, for example, a wavelength of from about 200 nm to about 1,500 nm. The coherent light source can be a laser. For example, an argon ion laser operating simultaneously at one or more visible lines can be used for excitation, although other light sources and wavelengths can be used. Exemplary excitation wavelengths include 488 nm and 514 nm. A pure output laser, for example, a laser emitting light of a single wavelength, can be a useful light source. Alternatively, the wavelength of the laser can be chosen or manipulated by use of an interference filter, a glass prism, or another filtering device as known to those skilled in the art of optics.

According to various embodiments, other devices can be used in addition to or instead of a substrate including separation channels. Devices can include, for example, a capillary array and sample retaining units. The sample retaining units can be a plurality of wells or vials. The sample retaining units can include a plurality of wells or vials. The sample retaining units can be affixed to a substrate or can be molded such that the substrate and the sample retaining units are a monolithic structure. For example, the substrate and the sample retaining units can be similar in form and shape to a standard 96-well reaction plate, available from Applied Biosystems, Foster City, Calif. The sample retaining units can be a plurality of individual vials that are placed in a substrate. The sample retaining units can be an array of wells, such as a 96-well reaction plate, for example, that is placed in a substrate.

According to various embodiments, a solid state laser can be used as a light source. Lasers produce monochromatic, coherent, directional light, providing a narrow wavelength of excitation energy. Solid state lasers use a lasing material which is distributed in a solid matrix, as opposed to using a gas, dye, or semiconductor, lasing source material. Examples of solid state lasing material include Ruby (694 nm), Nd:Yag (1064 nm), Nd:YVO$_4$ (1064 nm or 1340 nm, or doubled to emit at 532 nm or 670 nm), Alexandrite (655–815 nm), and Ti:Sapphire (840–1100 nm). Other solid state lasers known to those skilled in the art, including laser diodes, can also be used. The appropriate lasing material can be selected based on the desired wavelength. The laser can be selected to closely match the excitation wavelength of a fluorescent material in a sample in one or more channels. The operating temperature of the system also can be considered in selecting a laser because the emitted wavelength of a laser can be affected by the temperature, as known to those of ordinary skill in the art. The light source for the laser can be any source as known to those skilled in the art, for example, a flash lamp. Useful information about various solid state lasers can be obtained, for example, from www.repairfaq.org/sam/lasersl.htm. Examples of solid state lasers used in various systems for identification of biological materials include U.S. Pat. No. 5,863,502 to Southgate et al., and U.S. Pat. No. 6,529,275 B2 to Amirkhanian et al., both of which are incorporated herein in their entireties by reference.

The beam of coherent light can be focused and collimated through a collimating focusing lens interposed between the coherent light source and the channel array. For example, the excitation beam can be collimated to have a diameter of less than about 300 micrometers, for example, less than about 75 micrometers or less than about 50 micrometers, while traversing the channels in the array. According to various embodiments including an array comprising about 96 channels, the array width can be less than about 1.5 cm, and a lens with a focal length of from about 5 cm to about 30 cm, for example, about 10 cm, can focus and collimate the beam of coherent light such that the beam diameter remains less than about 75 micrometers while in the channels.

According to various embodiments, the focused line of the laser can be altered with a beam expander in order to irradiate a large number of channels. For example, the laser beam can be expanded perpendicular to the channel array. Such lengthening or "fanning out" of the laser line can facilitate positioning of the beam so that all channels are adequately irradiated. The beam can optionally be altered or redirected by use of a mirror, a filter, a lens, another optical element, or a combination thereof, prior to contacting the array. For example, mirrors can be used to provide a convenient means for adjusting the direction of the laser beam to be coplanar with the channel array and perpendicular to the channels. The use of mirrors, filters, lenses, or any combination thereof, is optional.

The transparent path can be optically coupled to a location external to the channel array. The location is to be broadly understood as any point, line, or plane, external to the array, including a single pixel, linear array of pixels, or planar array (two-dimensional array) of pixels. For example, the location external to the channel array can be a planar surface parallel to or angled with respect to the channel array. The location external to the channel array can include an optical detector capable of detecting fluorescence emissions from a target species in a sample in a channel of the channel array. The optical detector can be a two-dimensional image array detector. For example, the optical detector can be a charge-coupled device (CCD) or a charge-injection device (CID).

Referring now to the drawings, FIG. 1 is a perspective view of an embodiment of an electrophoresis device 12. Device 12 can include a plurality of separation channels, such as elongate channels 14, with each channel having an inlet end 16 and an outlet end 18. A first lead wire 22 connects a power source 20 with a first electrode (not visible in FIG. 1) disposed in electrical communication with the inlet ends 16 of the separation channels 14. A second lead wire 24 connects source 20 with a second electrode (not visible in FIG. 1) disposed in electrical communication with the outlet ends 18 of the separation channels 14. In operation, a voltage is applied between the first and second electrodes, and thereby along the channels 14, such that a sample zone is transported from the inlet ends 16, to the outlet ends 18 of the channels 14, and through an on-channel detection zone 30 located between the inlet ends 16 and the outlet ends 18.

Device 12 can be comprised of upper plate 26 and lower plate 28, with abutted confronting faces. As shown, lower plate 28 includes end portions 28a and 28c, and lateral side portions 28b and 28d. Lower plate 28 is provided with a plurality of non-intersecting elongate grooves, each of approximately semi-circular or semi-oval cross-section, positioned at regular intervals, for example, at a pitch of about 250 μm, and extending along a first face, for example, for a length of about 5 cm. The grooves can, at least in part, define separation channels 14. A first face of plate 26 is substantially planar, and, when disposed against the first face of plate 28 as shown in FIG. 1, further defines channels 14. In the illustrated arrangement, the grooves of plate 28 define lower boundaries (a floor) and sidewalls of each channel 14, and the first face of plate 26 provides an upper wall or ceiling for each channel 14.

According to various embodiments, both the upper and lower plates can be provided with complimentary sets of grooves that can be aligned with one another so that corresponding upper and lower grooves cooperate to define a plurality of elongate channels.

Instead of providing grooves in a lower plate which are covered by a planar first face of an upper plate, such as shown in FIG. 1, the device of the invention can include an upper plate with grooves formed along a first surface, which can be placed over a planar first surface of a lower plate (that is, essentially, the reverse of what is shown in FIG. 1). Although the device of the invention is illustrated as operating with the major planar surfaces of the plates disposed in a substantially horizontal fashion, the device can be configured to operate with the plates disposed substantially vertically, or tilted at a desired angle.

While the channels depicted in FIG. 1 are parallel to one another, it should be appreciated that other configurations are possible. The channels can converge toward one end of the device such that the distance separating adjacent channels (i.e., the pitch) becomes smaller along a direction towards the outlet ends. The central longitudinal axes of the channels can be straight, curved, or a combination thereof. Each channel can diverge to form two or more pathways having a common inlet end, a common outlet end, one or more common portion of a pathway, or a combination thereof. The channel can diverge horizontally, vertically, at an angle, or a combination thereof.

In the embodiment shown in FIG. 1, the flow cross-area, which is the cross-section taken perpendicular to the direction of sample migration, can be substantially the same for each channel. The channels shown in FIG. 1 all can be of a uniform depth as measured from the first face of the upper plate bounding a top region of the channel to the lowermost point, or floor, of the channel groove. Such uniformity can be achieved as the ordinary result of common microfabrication methods employed in constructing the device, such as etching. However, the invention additionally contemplates channels of varying depths, which can be made, for example, by use of a two stage etching process with multiple masks, or by other methods known to those skilled in the art of microfabrication. Each channel can have the same or a different depth as at least one other channel. The depth of each channel can vary along the length of the channel.

In practice, a separation medium can be injected by pressure or vacuum aspiration, or can be otherwise provided, in one or more separation channels to effect electrophoretic separation of the components of the sample(s). Any suitable injection technique can be used without limitation, including electrokinetic injection, hydrodynamic injection, injection by cross tee injector or double tee injector, or other injection method known to those skilled in the art of injection. According to various embodiments, the separation medium can be a flowable, non-crosslinked polymer solution.

As shown in FIG. 1, an excitation-beam source 34 can be provided for stimulating emission from sample zones located in detection zone 30. In an embodiment, the light source is a laser, for example, an argon ion laser, or a solid-state laser. Any suitable beam source can be used. As described in more detail below, according to an embodiment of the present invention, an excitation-beam pathway or path can extend through detection zone 30. An energy beam 48 generated by the beam source can pass along the excitation beam pathway. The beam pathway can be located between the inlet and outlet ends. The beam pathway can extend along a plane defined by the channels such that the beam pathway is co-planar with the plane of the channels. The beam pathway can be perpendicular to the direction of sample migration across the detection chamber. The beam pathway can approach the detection chamber at an angle with respect to the direction of sample migration. The beam passing along the beam pathway can be capable of simultaneously exciting plural sample zones in respective (different) channels.

According to various embodiments and as shown in of FIG. 1, the beam can enter a lateral side 28b of lower plate 28, pass through plate 28 including each of channels 14, and exit at an opposite lateral side 28d of plate 28. A laser dump or sink can be incorporated into plate 28, for example, proximate a region of side 28d, to terminate the beam after the beam passes through the channels.

As previously mentioned, a first electrode (not visible in FIG. 1) is in electrical communication with inlet ends 16 of separation channels 14. During operation of device 12, the first electrode can be maintained at a first voltage V using power source 20. Electrical communication between the first electrode and the inlet ends 16 of the separation channels 14 can be established, for example, by providing an electrically conductive solution in a reservoir/loading region 35 of device 14 so that both the inlet ends 16 of the channels 14 and the first electrode are in contact with the conductive solution.

As shown in FIG. 1, each channel 14 communicates with a second reservoir 37 through a respective outlet end 18. The reservoir can be located proximate the outlet ends 18.

The second electrode (not visible in FIG. 1) can be in electrical communication with outlet ends 18 of separation channels 14. During operation of device 12, the second electrode can be maintained at a second voltage V also using power supply 20. Electrical communication between the second electrode and second reservoir 37 can be established by providing an electrically conductive solution in second reservoir 37, such that the second electrode and outlet ends 18 are in contact with the conductive solution.

The electrodes used in the device can be formed from any electrically conducting materials. The electrodes can be made from a chemically inert material, for example, platinum, gold, stainless steel, or other relatively inert conductive materials. According to various embodiments, electrodes, for example, platinum electrodes, can be fabricated on the top or bottom plate by RF sputtering and/or photolithography before the top plate is bonded to the bottom plate.

The electrically conductive solution used to establish electrical continuity throughout the system can be any fluid capable of transporting an electrical current. For example, the conductive solution can be an ionic solution, for example, an aqueous solution containing a dissolved salt. In various embodiments, the conductive solution includes a buffer for stabilizing the pH of the solution. According to various embodiments, the ionic composition of the conductive solution can be the same in each of the separation channels, each of the electrode reservoirs, the detection chamber, or any combination thereof.

To facilitate optical detection of sample zones in the detection zone 30, part or all of a region in upper plate 26 covering detection zone 30 can be formed from a material which efficiently transmits light, such as an optically clear material, for example, glass, quartz, clear plastic, or an optically clear polymer film. To facilitate the introduction of an excitation light beam 48 into the detection zone to excite fluorescence of sample zones therein, part or all of the lower plate 28 along a region between the beam source 34 and the endmost channel 14 closest to the beam source 34 can be formed from a material which efficiently transmits light, for example, glass, quartz, clear plastic, or an optically clear polymer. According to various embodiments, the light-transmitting material does not significantly scatter light, and/or has little intrinsic fluorescence.

As shown in FIG. 1, a detector 38 is provided for detecting sample zones passing through the detection zone 30. The detector can be any type of detector for detecting emission of any type of radiation, for example, radioactivity, fluorescence, phosphorescence, chemi-luminescence, or a combination thereof. Detector 38 is capable of detecting fluorescence from a plurality of locations independently and/or simultaneously. Detector 38 can be, for example, a CCD camera, an array of photomultiplier tubes, a diode array, another detector means as known to those skilled in the art, or a combination thereof. As illustrated in FIG. 1, detector 38 can be connected to a computer 42 to store, analyze, and display data collected by the detector and/or to control the operation of the detector and other aspects of the device, as desired. For example, computer 42 can be programmed to control power source 20 and/or beam source 34.

In regions of the device where it is not required and/or desired for radiative emissions to be able to pass through, non-optically clear materials can be used. For example, non-optically clear regions can include polymeric materials, for example, Teflon or silicone.

The detection zone, as previously mentioned, can permit light to pass from each channel to the next channel, and from each channel to the detector. As previously mentioned, the detection zone can include a substantially or partially transparent region of one or more channels. According to various embodiments, the detection zone can include a substantially transparent region of each channel sidewall, wherein the transparent regions form a substantially linear path for passage of the excitation beam therethrough. Alternatively, the detection zone and/or excitation beam pathway can include a channel transverse to each of the plurality of channels and passing therethrough, such that the beam is substantially linear and passes through each channel without passing through sidewalls between channels.

The device can include one or more additional elements capable of conducting capillary electrophoresis. For example, the device can include a temperature control device for controlling the temperature of the separation channels. Details of these and other common features of an operable capillary electrophoresis device can be found in any number of available publications, including Capillary Electrophoresis Theory and Practice, Grossman and Colburn, eds., Academic Press (1992), incorporated herein in its entirety by reference.

Various embodiments can provide for reduced crosstalk between channels while not inhibiting excitation of the one or more fluorescent dye in the sample, or detection of the emitted light therefrom. For example, bandpass filters that transmit light only within a defined spectral band can be used. An excitation filter can be employed such that only light capable of exciting a reporter of interest strikes the sample. For example, an excitation filter can be coated on or fixed to one or more desired regions of the lower plate. An emission filter can be employed such that the fluorescence from the sample passes to a detector while stray light from the light source or interfering components in the sample can be blocked. For example, an excitation filter can be coated on or fixed to one or more desired regions of the upper plate.

Figure 2A:
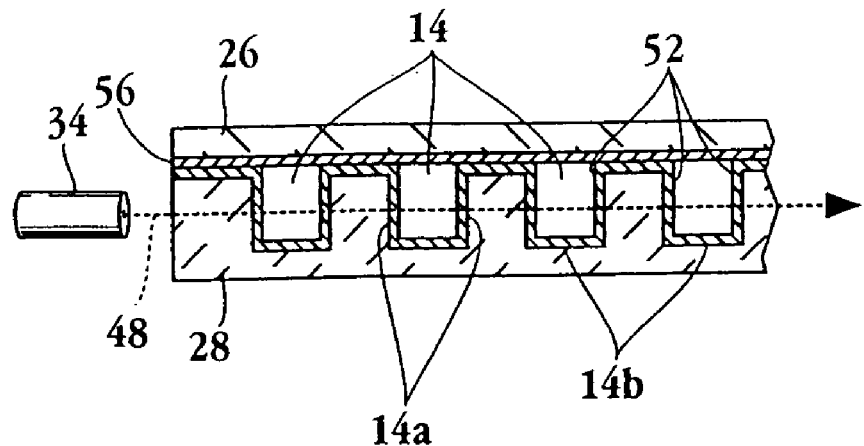
FIGS. 2A, 2B, and 2C are partial, cross-sectional views of multi-channel analyte separation devices, according to various embodiments.
Figure 2B:
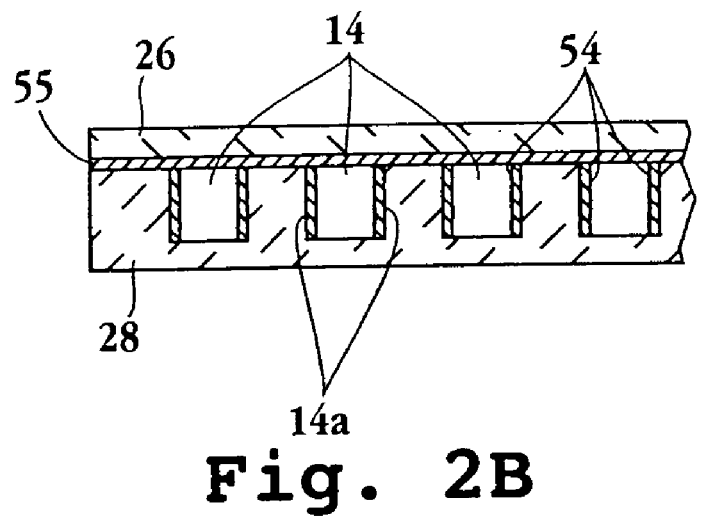
Figure 2C:
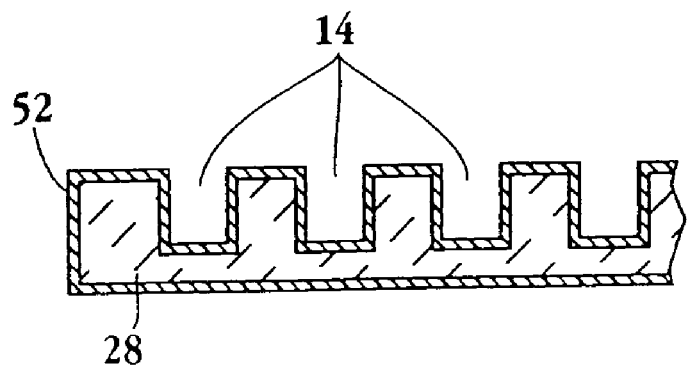
Figure 3A:
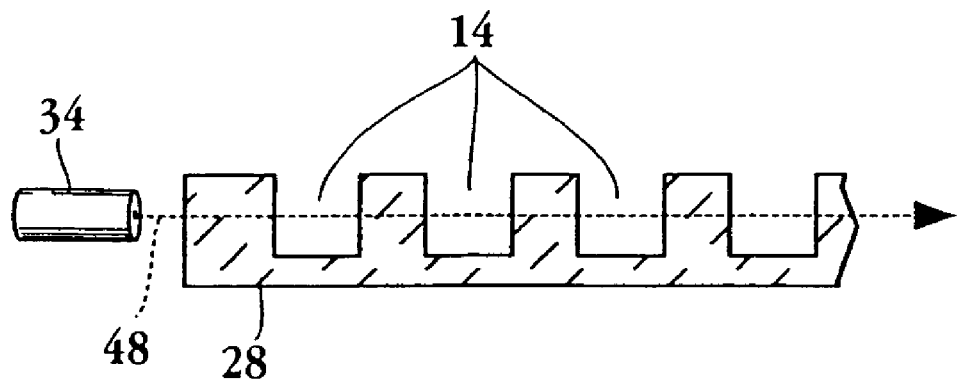
FIGS. 3A, 3B, and 3C are cross-sectional views of substrates with channels formed therein having various geometries, according to various embodiments.
Figure 3B:
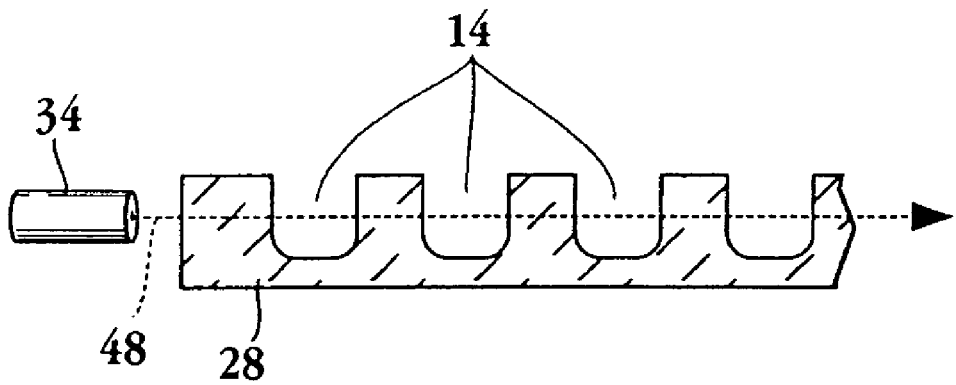
Figure 3C:
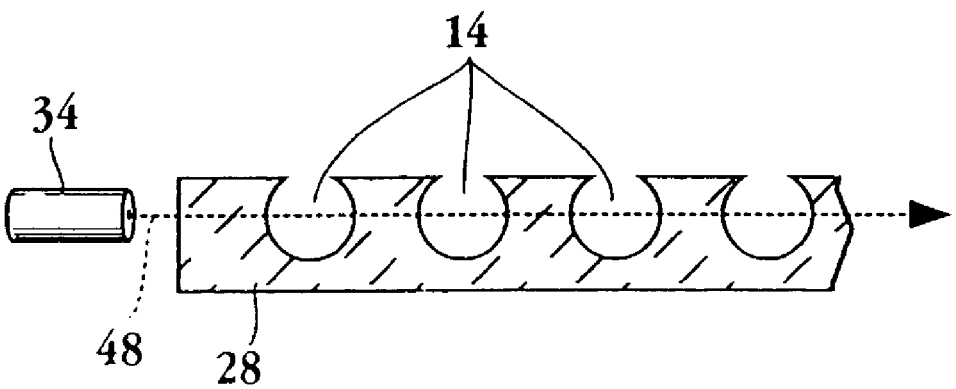

According to various embodiments and as depicted in the sectional views of FIGS. 2A–C, a lower glass or plastic plate 28 can be provided with spaced-apart etched channels 14. While each channel 14 is shown having vertical sidewalls 14a and a flat bottom or floor region 14b, which meet at ninety-degree angles, other channel geometries can be employed, as shown, for example, in FIG. 3.

The sidewalls 14a of the channels can have bandpass characteristics that substantially only permit passage of the excitation (laser) beam 48 through the device. For example, a coating material 52 can be applied to the channel sidewalls 14a and, optionally, the floor regions 14b (see FIG. 2A); micro-optical elements 54 can be attached on each sidewall 14a (see FIG. 2B); the whole lower etched plate, including the channels in their entireties, can be coated with a bandpass coating 52 permitting only excitation light to pass through (see FIG. 2C); or a combination thereof. An upper or cover plate 26, overlaid over the channels 14, can be provided with bandpass characteristics that allow only sample emission (for example, fluorescence) wavelengths to pass through, and can prevent the passage of excitation beam wavelengths. For example, a bandpass coating material 56, as shown in FIG. 2A, can be applied to one or more face regions of the upper plate 26 that face the lower plate 28 and channels 14, at least along regions along the detection zone. A micro-optical bandpass element 55 as shown in FIG. 2B can be attached to the face of upper plate 26 confronting lower plate. Optical elements and coatings useful in connection with the present teachings are described, for example, in U.S. Pat. Nos., 3,466,120; 6,112,005; 5,872,655; 4,663,557; 6,100,541; each of which is incorporated herein in its entirety by reference.

According to various embodiments, bandpass characteristics permitting passage of the excitation laser beam 48 through the device, and preventing the passage of excitation beam wavelengths between channels, can be achieved by dyeing, doping, impregnating, mixing, compositing, or coating the material of the channel sidewalls 14a, and/or the material of the channel bottom or floor region 14b, with a light-absorbing and/or light-quenching material, for example, with a non-fluorescent quencher (NFQ). An NFQ is a dye that absorbs fluorescent light of a particular wavelength, and does not itself emit a fluorescent wavelength. As used herein, the term "light-absorbing and/or light-quenching material" is meant to include any dye, pigment, colorant, or other radiatively absorptive material that is capable of absorbing one or more ranges of wavelengths. According to various embodiments, the light-absorbing and/or light-quenching material can allow a first range of wavelengths to pass through. The use of one or more NFQ in the channel sidewalls and/or bottom can help to prevent or eliminate optical cross-talk between the channels. One or more NFQ can be incorporated into material of the sidewalls and/or bottom of the channel, or can be coated thereon.

According to various embodiments wherein at least one NFQ is coated on the sidewalls and/or bottom of a channel, the channel material can be coated with an NFQ dye-containing photoresist. The coated material can be exposed to light, while the remaining material can be protected, for example, by a mask. The photoresist can then be developed, retaining the light-exposed portions of the coating on the channel material. The coated portions of the channel material can optionally be coated with a conformal coating, for example, an acrylic, a urethane, an epoxy, a silicone, or a poly-para-xylylene, for example, Parylene, coating. According to various embodiments, the light-absorbing and/or light-quenching coated portions of the channel material can be coated with Parylene. The NFQ coating can be present on one or more portion of one or more sidewall, bottom region, or ceiling, of one or more channels. One or more portions of a channel or all of a channel, can be coated. For example, at least a portion of a channel within the detection zone and/or excitation beam pathway can be coated. The coating can be of any suitable thickness, for example, from about 0.01 mil to about 20 mils, or from about 0.1 mil to about 10 mils thick. The coating can be from about 2 mils to about 5 mils thick.

According to various embodiments, the light-absorbing and/or light-quenching material can be incorporated into the substrate and/or cover material. For example, one or more NFQ can be mixed with a substrate material while the material is in powdered, beaded, liquid, molten, or unreacted or uncured form. For example, the concentration of the NFQ can be from about 0.01 percent to about 20 percent of the total volume of the mixture of the NFQ and the substrate material. For example, the concentration of the NFQ can be from about 1 percent to about 5 percent. The NFQ-containing material can then be formed into a substrate, or a portion of a substrate, such as a substrate bottom, a sidewall, or a cover. If the material is formed into a bottom or sidewall, the bottom and/or sidewall can be attached to remaining portions of the substrate by any method known in the art, for example, by use of an adhesive, or a hot-melt adhesive, or by thermal bonding, chemical bonding, heat fusion, or the like. The light-absorbing and/or light-quenching material can form all or a portion of a bottom, sidewall, or cover of one or more channels. More than one light-absorbing and/or light-quenching material, or more than one light-absorbing and/or light-quenching material, or more than one NFQ, can be used in a single substrate material.

According to various embodiments, the light-absorbing and/or light-quenching material can be injected into the substrate after the substrate has been formed. For example, one or more NFQs can be injected into alternating capillaries in a capillary array. For example, one or more NFQs can be injected or placed into alternating channels in a channel array. For further example, one or more NFQs can be injected or placed into alternating wells in a plate of wells or vials. The NFQ can be mixed with an aqueous solution, a gel, or a polymer prior to injection or placement. For example, one or more NFQs can be mixed with a pre-polymerized monomer solution, the mixture can be injected into alternating capillaries, and the mixture can be polymerized. The mixture can be polymerized prior to injection into alternating capillaries. For example, one or more NFQs can be mixed with an aqueous solution and placed in alternating wells or vials in a plate or holder. The concentration of the NFQ can be from about 1 percent to about 50 percent of the total volume of the mixture of NFQ and the carrier solution. For example, the concentration of the NFQ can be from about 10 percent to about 50 percent.

According to various embodiments, an NFQ dye can be used as the light-absorbing and/or light-quenching material. The NFQ dye can be selected for use based on the reporter used in the sample. Where one or more reporter is used in a sample, one or more corresponding NFQ dye can be used to coat, or can be used in the material of, one or more portions of a corresponding channel for the sample. The portion or portions can include one or more portions of a sidewall of the channel, a bottom region of the channel, a ceiling of the channel, or a combination thereof. The one or more NFQ dye can pass light of the excitation frequency, or can pass light of the emission frequency, of one or more reporter, and can prevent passage of at least a substantial portion of one or more other wavelengths of light. For example, where the reporter is FAM, suitable NFQs for blocking the emission wavelength of FAM from regions between channels can include Methyl Orange, Disperse Red 13, Basic Violet 14, Basic Red 9, and other non-fluorescent dyes having an absorbance with a λ-max at about 520 nm. If the reporter is ROX, suitable NFQs for blocking the emission wavelength of ROX between channels can include Malachite Green, Ethyl Violet, Fast Green FCF, Brilliant Green, Crystal Violet, and other dyes known to those skilled in the art to absorb with a λ-max at about 605 nm. If more than one reporter is used, an NFQ dye capable of substantially absorbing wavelengths at about the λ-max of one or more of the reporters can be used. For example, if both FAM and ROX are used as reporters, Crystal Violet can be used as the NFQ because it substantially absorbs light at both 520 nm and 605 nm. The λ-max can vary or can be adjusted in response to or to compensate for the substance or substrate that the light travels through.

By these or similar arrangements, excitation light can be permitted to pass laterally through the device in a side-entry, on-channel configuration while substantially excluding light of other bandwidths. Fluorescent emissions from sample zones can be permitted to pass out of the channel to a detector while substantially excluding light of other bandwidths.

A number of commercial entities produce a wide range of coating technology products that can find use with the teachings herein, including bandpass filters, beamsplitters, reflectors, collectors, and sputtered metals. Such entities include, for example, Seoul Precision Optics Co., Korea; GM Vacuum Coating Laboratory, California, a division of Navitar Coating Labs; Optical Coating Laboratory, Inc., California a JDS Aniphase Company; and Guernsey Coating Laboratories Inc., California.

Figure 4:
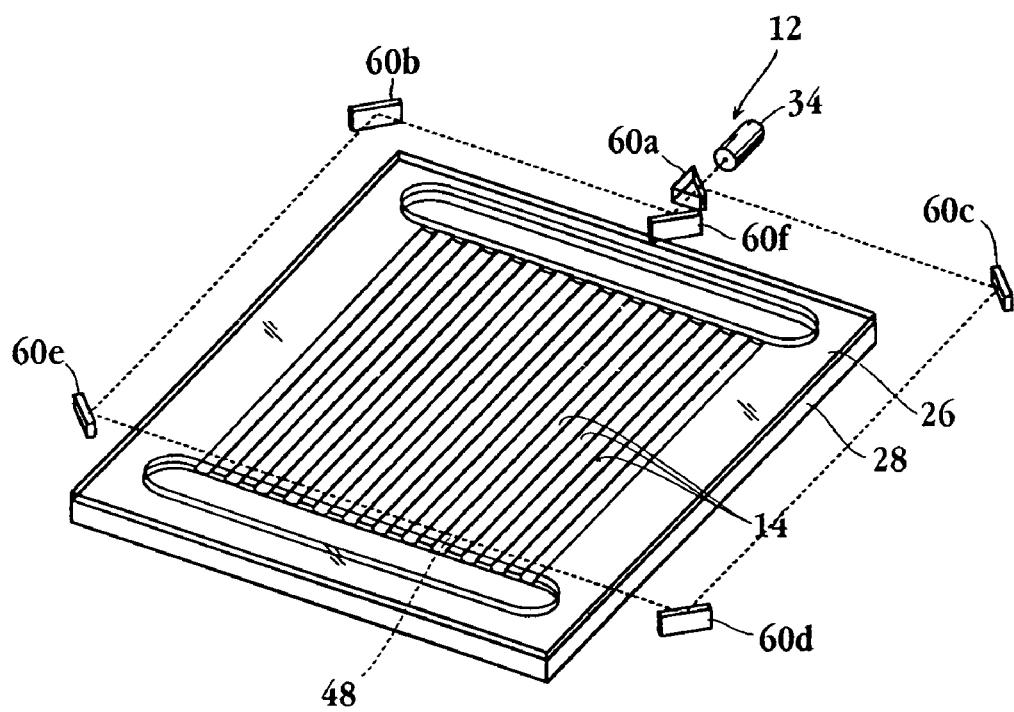
FIG. 4 is a perspective view from above of an electrophoresis system, including a multi-channel analyte-separation device including a plurality of separation channels, an excitation beam source, and optics directing an excitation beam for entry into the channel device from each lateral side thereof, according to various embodiments.

According to various embodiments, an excitation beam of light can be directed toward the array from each lateral side of the device. For example, two lasers can be employed, one on each side of the device. Alternatively, as depicted in FIG. 4, a single laser source 34 can be employed in combination with appropriate beam splitting 60a and directing optics, for example, mirrors 60b–e, so that light enters the array from each lateral side of the device.

In some instances, less than all of the channels provided by the device can be used to conduct separations. For example, the left- and right-endmost channels might not be loaded with samples, while the remaining channels are so loaded, or every other channel might be utilized, with the intervening channels remaining unused. Other sample loading configurations as known to those skilled in the art, are also envisioned.

All publications, patents, and patent applications, referred to herein are hereby incorporated by reference to the same extent as if each individual publication, patent, or patent application, was specifically and individually indicated to be incorporated in its entirety by reference.

Those skilled in the art can appreciate from the foregoing description that the broad teachings herein can be implemented in a variety of forms. Therefore, while the devices, systems, and methods herein have been described in connection with particular embodiments and examples thereof, the true scope of the present teachings should not be so limited. Various changes and modifications can be made without departing from the scope of the present teachings.

What is claimed is:

1. A device for the analysis of one or more samples, comprising:
   a substrate;
   a plurality of adjacently arranged channels formed in the substrate, with each channel having an inlet end and an outlet end, the channels being disposed spaced apart from one another, with each adjacent pair of channels being separated by a respective portion of the substrate that includes at least a region that is transparent and at least a region that comprises a non-fluorescent quencher; and
   an excitation-beam source adapted to direct an excitation beam of light along a beam path that intersects each of the channels at a region between the inlet and outlet ends and further intersects the transparent region of the substrate separating adjacent pairs of channels.

2. The device of claim 1, further comprising a cover member positioned adjacent the substrate, over the channels.

3. The device of claim 2, further comprising an emission detection system optically coupled to a region within each channel along the beam path.

4. The device of claim 1, wherein the substrate is a plate, slide, wafer, or chip comprised at least in part of an optically clear material.

5. The device of claim 1, wherein the substrate is a monolithic structure.

6. The device of claim 1, wherein the substrate is a multi-laminate structure.

7. The device of claim 1, wherein each channel includes opposed sidewall regions including portions that are substantially parallel to one another.

8. The device of claim 7, wherein the transparent region comprises, at least in-part, the parallel portions, and wherein the beam path extends through the parallel portions.

9. The device of claim 1, further comprising a coating on one or more portion of the plurality of separation channels, wherein the coating includes the non-fluorescent quencher.

10. The device of claim 1, wherein the non-fluorescent quencher is incorporated into the substrate.

11. The device of claim 1, wherein at least a portion of one or more of the plurality of separation units comprises a reporter dye, wherein the reporter dye includes FAM, and wherein the non-fluorescent quencher includes at least one of Methyl Orange, Disperse Red 13, Basic Violet 14, Basic Red 9, and non-fluorescent dyes having an absorbance with a $\lambda$-max at about 520 nm.

12. The device of claim 1, wherein at least a portion of one or more of the plurality of separation units comprises a reporter dye, wherein the reporter dye includes ROX and wherein the non-fluorescent quencher includes at least one of Malachie Green, Ethyl Violet, Fast Green FCF, Brilliant Green, Crystal Violet, and non-fluorescent dyes having an absorbance with a $\lambda$-max at about 605 nm.

13. The device of claim 1, wherein at least a portion of one or more of the plurality of separation units comprises a plurality of reporter dyes and a plurality of non-fluorescent quenchers, wherein the plurality of non-fluorescent quenchers includes at least two non-fluorescent quenchers with different $\lambda$-max absorbance values.

14. A device for the analysis of one or more samples, comprising:
a substrate including one or more regions, the one or more regions including a material that comprises a non-fluorescent quencher;
a plurality of adjacently arranged channels formed in the substrate, wherein each channel includes an inlet end and an outlet end and the channels are disposed in spaced relation to one another, with each adjacent pair of channels being separated by a respective portion of the substrate;
a transverse channel in the substrate transverse to and passing through each of the plurality of adjacently arranged channels in the substrate; and
an excitation-beam source adapted to direct an excitation beam of light along a beam path that intersects each of the channels at a region between the inlet and outlet ends, wherein the beam path is along the transverse channel.

15. The device of claim 14, wherein at least a portion of the substrate in each of the separation channels includes a non-fluorescent quencher dye.

16. The device of claim 14, wherein the separation channels are non-intersecting.

17. The device of claim 14, wherein the substrate is a plate, slide, wafer, or chip; and wherein the separation channels are microfabricated therein.

18. A device for the analysis of one or more samples, comprising:
a plurality of sample-containment units, each sample-containment unit including an open end and a closed end and an interior portion between the ends;
an excitation source adapted to direct an excitation beam of light along a beam path that intersects the interior portion of each of the sample-containment units at a region between the open and closed ends; and
an emission detection system optically coupled to the interior portion of the separation units, in the vicinity of the beam path,
wherein at least a portion of one or more of the plurality of sample-containment units comprises a non-fluorescent quencher.

19. The device of claim 18, further comprising an optical coating or element on one or more regions of the sample-containment units.

20. The device of claim 18, further comprising a cover member positioned over the sample-containment units.

21. The device of claim 20, further comprising an optical coating or element on the cover.

22. The device of claim 18, wherein each sample-containment unit is continuous from its open end to its closed end.

23. The device of claim 18, wherein the units comprise separate respective sample vials.

24. The device of claim 18, wherein the excitation-beam source comprises at least one laser.

25. The device of claim 24, wherein the device further comprises a substrate, the substrate comprises first and second lateral sides, the beam path extends between the first and second lateral sides, and at least one laser is configured to emit a beam that enters the device along the beam path from each of the first and second lateral sides.

26. The device of claim 25, wherein the substrate includes a transparent region between the first and second lateral sides, and the beam path extends along the transparent region.

27. The device of claim 18, wherein each sample-containment unit includes opposed sidewall regions including portions that are substantially parallel to one another.

28. The device of claim 27, wherein the beam path extends through the parallel portions.

29. The device of claim 28, wherein the parallel portions, through which the beam path extends, are transparent to at least a selected wavelength range of light.

30. The device of claim 18, wherein the device further comprises a substrate, and the substrate includes at least one transverse channel transverse to and passing through at least some of the plurality of units, and wherein the beam path extends through the transverse channel.

31. The device of claim 18, wherein the non-fluorescent quencher is coated on one or more portion of one or more of the plurality of separation units.

32. The device of claim 18, wherein the non-fluorescent quencher is incorporated into the sample-containment units.

33. The device of claim 18, further comprising a substrate, wherein the sample-containment units are an array of sample-containment units that are adapted to be placed into the substrate.

34. A method of forming a device, comprising:
providing a substrate material and a non-fluorescent quencher;
forming a substrate from the substrate material and the non-fluorescent quencher, wherein the substrate includes a plurality of adjacently arranged channels, each channel having an inlet and an outlet end, the channels being disposed in spaced relation to each other.

35. The method of claim 34, further comprising coating at least a portion of the substrate with a coating material, wherein the coating material comprises the at least one non-fluorescent quencher.

36. The method of claim 34, further comprising:
mixing the substrate material with the at least one non-fluorescent quencher.

37. The method of claim 34, further comprising:
retaining one or more non-fluorescent quenchers in alternating channels of the plurality of adjacently ranged channels.

38. A method of forming a device, comprising:
providing a substrate material and a non-fluorescent quencher;
forming a substrate from the substrate material and the non-fluorescent quencher, wherein the substrate includes a plurality of adjacently arranged separation units, each separation unit having an inlet and an outlet end, the separation units being disposed in spaced relation to each other.

39. The meted of claim 38, further comprising coating at least a portion of the substrate with a coating material, wherein the coating material comprises the at least one non-fluorescent quencher.

40. The method of claim 38, further comprising:
mixing the substrate material with the at least one non-fluorescent quencher.

41. The method of claim 38, further comprising:
retaining one or more non-fluorescent quenchers in alternating separation units.

* * * * *

UNITED STATES PATENT AND TRADEMARK OFFICE
CERTIFICATE OF CORRECTION

| | |
|---|---|
| PATENT NO. | : 7,019,831 B2 |
| APPLICATION NO. | : 10/623913 |
| DATED | : March 28, 2006 |
| INVENTOR(S) | : Paul D. Grossman et al. |

Page 1 of 1

It is certified that error appears in the above-identified patent and that said Letters Patent is hereby corrected as shown below:

Claim 37 - Col. 17 Line 10 "ranged" should read --arranged--

Claim 39 - Col. 18 Line 5 "meted" should read --method--

Signed and Sealed this

Third Day of April, 2007

JON W. DUDAS
*Director of the United States Patent and Trademark Office*